United States Patent [19]
Lieber et al.

[11] Patent Number: 6,130,092
[45] Date of Patent: *Oct. 10, 2000

[54] RIBOZYME GENE LIBRARY AND METHOD FOR MAKING

[75] Inventors: Andre Lieber, Berlin, Germany; Michael Strauss, deceased, late of Berlin, Germany, by Irene Strauss, legal representative

[73] Assignee: Max-Planck Gesellschaft zur Förderung der Wissenschaften e.V.

[ * ] Notice: This patent is subject to a terminal disclaimer.

[21] Appl. No.: 08/887,674

[22] Filed: Jul. 3, 1997

Related U.S. Application Data

[63] Continuation-in-part of application No. 08/712,803, Sep. 12, 1996, abandoned, which is a continuation of application No. 08/314,587, Sep. 28, 1994, abandoned, which is a continuation-in-part of application No. 08/314,588, Sep. 28, 1994, Pat. No. 5,695,992.

[30] Foreign Application Priority Data

Jul. 4, 1994 [DE] Germany ............... 44 24 761
Jul. 4, 1994 [DE] Germany ............... 44 24 762

[51] Int. Cl.$^7$ ............... C12N 15/09; C12N 15/63; C12P 19/34; C12Q 1/68

[52] U.S. Cl. ............... 435/489; 435/6; 435/91.31; 435/320.1; 536/24.5

[58] Field of Search ............... 435/6, 29, 91.31, 435/320.1, 375, 489; 514/44; 536/24.5

[56] References Cited

U.S. PATENT DOCUMENTS 5,254,678 10/1993 Haseloff et al. ............... 536/23.3
5,496,698 3/1996 Draper et al. ............... 435/6
5,695,992 12/1997 Lieber et al. ............... 435/320.1

FOREIGN PATENT DOCUMENTS 2687411 8/1993 France .

OTHER PUBLICATIONS

J. Cell Biochem Sppl. O, vol. 17, No. E, 1993 "Design of Quasi–random Ribozyme Expression Vectors".

*Primary Examiner*—George C. Elliott
*Assistant Examiner*—Thomas G. Larson
*Attorney, Agent, or Firm*—Londa & Gluck LLP

[57] ABSTRACT

A ribozyme library which comprises a collection of ribozyme genes encoding a hammerhead structure and flanking sequences of random nucleotides cloned at least once into an expression cassette for ribozyme expression.

8 Claims, 7 Drawing Sheets

```
 841  AGGCGGGGATGGGGGAGACCTGTAGTCAGAGCCCCCGGCAGCACAGCCAATGCCCGTCC
 901  TTGCCCCTGCAGAACCTAGAGCTGCTCCGCATCTCCTGCTCATCCAGTCGTGGCTG
                                                            →E1
 961  GAGCCCGTGCAGTTCCTCAGGAGTGTCTTCGCAACAGCCTGGTGTACGGCGCCTCGAC
 1021 AGCAAGGTCTATGACCTCCTAAGGACCTAGAGGAAGGCATCCAAACGCTGATGGGGGTG
                    →I2
 1081 AGGGTGGCGCCAGGGGTCCCCAATCCTCGAGCCCCACTGACTTTGAGAGACTGTGTTAGA
                     →I1
 1141 GAAACACTGGCCTGCCCCTCTTTTTAGCAGTCAGGCCCTGACCCCAAGAGAACTCACCTTATT
 1201 CTTCATTCCCCTCGTGAATCCTCCAGGCCTTCTCTACACTGAAGGGAGGAGGAAAA
 1261 TGAATGAATGAGAAAGGGAGGAACAGTACCCAGCGCTTGGCCTCTCCTTCTCTTCCTT
 1321 CACTTTGCAGAGGCTGGAAGATGACCAACAACGATGACGCACTACTCAAGAATCTTCAAGCAGACCTA
 1381 CAGCAAGTTCGACACAAACTCACACAACGATGACGCACTACTCAAGAACTACGGCTGCT
           →E4                                              →E3
 1441 CTACTGCTTCAGGAAGGACATGACAAGGTCGAGACATTCCTGGCCATCGTGCAGTGCCG
 1501 CTCTGTGTGGAGGGCAGCTGTGCTTCTAGCTGCCGGGTGGCATCCCTGTGACCCCTCCCC
 1561 AGTGCCTCTCCTGGCCCACTCCAGTGCCACTCCAGTGCCCCAGCCTTGTCCTAATAAA
 1621 ATTAAGTTGCAT
```

FIG. 4

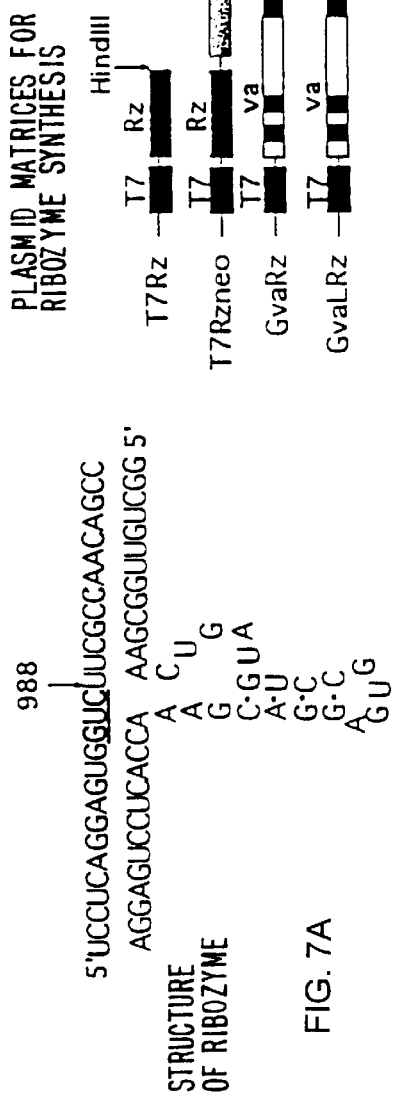
FIG. 7A STRUCTURE OF RIBOZYME
FIG. 7B PLASMID MATRICES FOR RIBOZYME SYNTHESIS
FIG. 7C ELECTROPHORETIC REPRESENTATION OF CLEAVAGE PRODUCTS

RIBOZYME GENE LIBRARY AND METHOD FOR MAKING

This application is a continuation-in-part of U.S. Ser. No. 08/712,803, filed Sep. 12, 1996 (now abandoned), which is a continuation of U.S. Ser. No. 08/314,587, filed Sep. 28, 1994 (now abandoned); and is also a continuation-in-part of U.S. Ser. No. 08/314,588, filed Sep. 28, 1994, now U.S. Pat. No. 5,695,992.

FIELD OF THE INVENTION

The present invention relates to a ribozyme library, its preparation and use. The library of the present invention contains ribozymes for desired target sequences for use in the fields of molecular biology, genetic engineering, and in medicine, by expression and in vivo and in vitro insertion, suitably for identification and switching off genes in the case of diseased conditions.

BACKGROUND OF THE INVENTION

The inactivation of gene functions by reverse genetic material is the most important method for switching off certain genes. This is of great importance for combating infectious and other diseases, including AIDS, caused by interference with gene expression. A gene function can be inactivated on various levels, by homologous recombination at the DNA level, by antisense nucleic acids or ribozymes on the RNA level, or by antibodies on the protein level. In conversion to practice, all of these possibilities have advantages and disadvantages. For therapeutic applications, only the RNA inactivation by antisense molecules or by ribozymes appears to be implementable. Both classes of compounds can be synthesized chemically or produced in conjunction with a promoter by biological expression in vitro or even in vivo. The principle of catalytic self-cleavage of RNA molecules and the cleavage in trans has become well established in the last 10 years. The hammerhead ribozymes are characterized best among the RNA molecules with ribozyme activity. Since it was shown that hammerhead structures can be integrated into heterologous RNA sequences and that ribozyme activity can thereby be transferred to these molecules, it seems clear that catalytic antisense sequences for almost any target sequence can be created provided the target sequence contains a potential cleavage site.

The basic principle of constructing ribozymes is quite simple. An interesting region of the RNA, which contains the GUC (or CUC) triplet, is selected. Two oligonucleotide strands, each with 6 to 8 nucleotides, are taken and the catalytic hammerhead sequence is inserted between them.

Molecules of this type were synthesized for numerous target sequences. They showed catalytic activity in vitro and in some cases also in vivo. The best results were obtained with short ribozymes and target sequences. A topical challenge for the in vivo application is the construction of ribozyme genes which permit a continuous expression of the ribozyme in a particular cell (Bertrand, E. et al., (1994) Nucleic Acids Res. 22, 293 to 300).

There are five possible causes for interference with a satisfactory functioning of expressed ribozymes within the complex intracellular milieu:

1. The mRNA substrate exists within the cell presumably in a highly folded structure, which can also be protected by proteins bound to parts of the structure. The encountering of accessible sites within the substrate allowing for hybridization with the complementary flanking regions of the ribozyme, is a question of actual probability. Computer aided predictions of possible, thermodynamically stable secondary structures can be useful when searching for loop regions without base pairing. However, the physiological relevance of these conformation models is still uncertain.
2. Since the target mRNA is transported immediately out of the cell nucleus, the ribozyme must also enter the cytoplasm, preferably along the same path. It is, however, difficult to achieve a co-localization of ribozyme and its substrate.
3. The in vivo use of ribozymes requires the insertion of ribozyme genes in suitable expression cassettes. The transcription of these constructs can produce mRNAs, in which the central, catalytic, secondary structure of the ribozymes is displaced by other, more stable base pairings within the non-complementary flanking sequences. Suitable expression cassettes can be constructed in accordance with the prior art, to express the ribozyme library.
4. A 100- to 1,000-fold excess of ribozyme molecules relative to the target sequence is necessary, for attaining a recordable increase in the RNA level. The production of 105 to 106 ribozymes per cell over a long period of time can, however, have cytotoxic effects. In general, such high expression levels are not stable. An excess of ribozymes is needed because of the inadequate stability of the ribozymes in the presence of nucleases, because of the ineffective transport to the cytoplasm and because of the less than optimum conversion factor of the cleavage reaction.
5. The kinetics of the cleavage reaction and the ability of the ribozymes to carry out multiple conversion reactions depends on the binding parameters and the structure of the complementary flanking regions of the ribozymes. Cellular proteins can affect the catalysis of the cleavage reaction, probably with the help of the dissociation of the ribozyme from the substrate of the cleavage reaction, which represents the preliminary step of the next cleavage reaction. Until now, it has not been possible to predict the optimum structure of the flanking regions for a ribozyme, to guarantee high specificity and high conversion. It can be noted that, despite many efforts to construct specific ribozyme genes, generally only partial successes have been achieved, mostly on the basis of trial and error experimentation. Expression cassettes useful in conjunction with the present invention and their preparation, are also described in:

Cameron F. H. and Jennings. P. A. (1989). Specific gene suppression by engineered ribozymes in monkey cells Proc. Natl. Acad. Sci. USA 86. 9139–9143.

Cotten M. and Birnstiel. M. L. (1989). Ribozyme-mediated destruction of RNA in vivo. EMBO J.8, 3861–3866.

Efiat s. Leiser. M. Wu. Y. J. Fusco-DeMane, D. Emran, O. A., Surana. M. Jetton. T. L., Magnuson, M. A. Weir C. and Fleischer, N (1994) Ribozyme-mediated attenuation of pancreatic B-cell glucokinase expression in transgenic mice results in impaired glucose-induced insulin secretion Proc. Natl. Acad. Sci. USA 91, 2051–2055.

Rossi J. J (1995), Controlled, targeted, intracellular expression of ribozyme; progress and problems. TIBTECH 13. 301–306.

Sioud M. and Drlica. K (1991). Prevention of human immunodeficiency virus type 1 integrase expression in *Eschenchia Coli* by a ribozyme. Proc. Natl. Acad. Sci. USA 88, 7303–7307.

Shore, S. K., Nabissa, P. M. and Reddy, E. P. (1993) Ribozyme-mediated cleavage of the BCRABL oncogene transcript; in vitro cleavage of RNA and in vivo loss of P210 protein-kinase activity. Oncogene 8. 3183–3188.

Steinecke, P. Herget. T. and Schreter, P. H. (1992). Expression of a chimeric ribozyme gene results in endonucleolytic cleavage of target mRNA and a concomitant reduction of gene expression in vivo EMBO J. 11. 1525–1530.

Thompson. J. D. Ayers, D. F. Malmstrom. T. A. McKenzie T. L. Ganousis. L. Chowrira. B. M. Couture, I, and Stinchcomb, D. T. (1995). Improved accumulation and activity of ribozymes expressed from a tRNA-based RNA polymerase III promoter. Nucleic Acids Res. 23. 2259–2268.

DESCRIPTION OF THE INVENTION

It is an object of the present invention to enable preparation of optimum ribozymes for any target sequence. It enables the effective expression of stable ribozymes, suitably for identifying and switching off genes in the case of illnesses.

The present invention is a ribozyme gene library, and a method for producing the ribozyme gene library wherein the desired target sequence, or that one that is to be switched off, itself searches out the most suitable ribozyme from a selection of ribozymes with known stability and structure. Pursuant to the present invention, this is accomplished due to the ribozyme library which can be expressed within any expression cassette. For example one can use a conventional polymerase II-promoter (e.g. cytomegalovirus CMV), a piece of a gene coding for mRNA, as well as a termination sequence. Another way of expressing the ribozyme library is a conventional polymerase I-gene with a promoter and a termination sequence. Yet another way is a polymerase III-gene with an internal promoter (e.g. the VA-RNA gene).

However, the biological activity of the ribozyme requires a secondary structure formation which is correctly formed on one side of the ribozyme structure, and on the other side prevents the flanking DNA sequences from a structural inhibition of the ribozyme activity. The conventional expression cassettes of the three above-exemplified types enable the expression of all ribozyme genes in the library, but they can have an unpredictable effect on the folding of individual ribozyme-RNAs. An expression cassette can be optimized, containing from about $10^9$ to about $10^{11}$ ribozyme genes, and the expression cassette suitably contains a T7 promoter, an adenoviral va-RNA-gene, and a stable loop region to assure an open structure of the ribozyme sequences. These ribozymes have a central hammerhead structure of defined sequence and flanking sequences of bases arranged randomly. The hammerhead structure is coded by a double stranded gene, in which the hammerhead is enclosed on both sides by flanking, random sequences of bases.

An analogous library can also be created with other antisense genes.

DESCRIPTION OF THE DRAWING

The invention is described in detail, with reference being had to the drawing, wherein:

FIG. 4 is the partial nucleotide sequence of the hGH gene;

FIGS. 7A–C show the result of cleavage of hGH RNA in vitro by a ribozyme. More specifically FIG. 7(A) shows the structure of ribozyme (SEQ ID NO: 12);

FIG. 7(B) shows plasmid matrices for ribozyme synthesis; and

FIG. 7(C) shows electrophoretic representation of cleavage products.

DETAILED DESCRIPTION OF THE INVENTION

Figure 1:
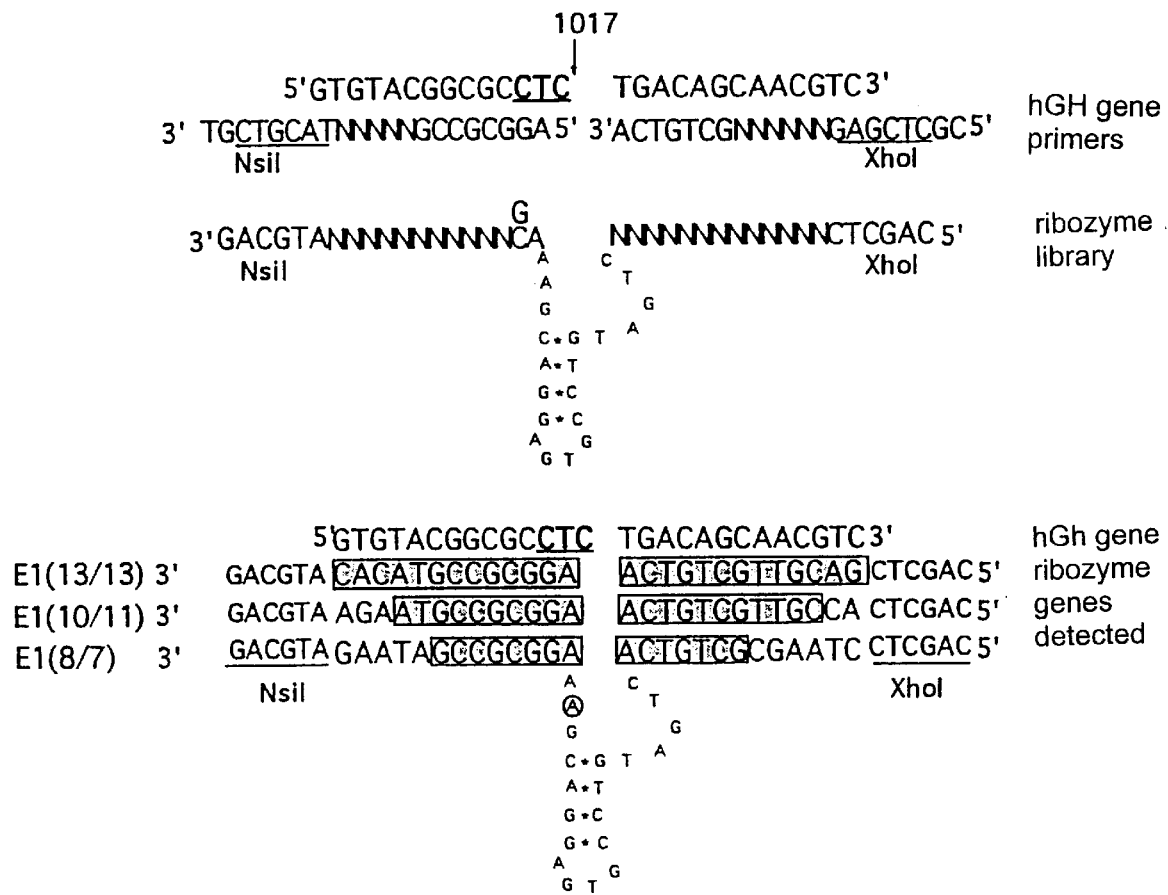
FIG. 1 shows the construction of the ribozyme library of the present invention (SEQ ID NO: 5,6)

The double-stranded hammerhead region suitably has the sequence CTGATGAGTCCGTGAGGACGAAAC (Seq. Id. No. 1) and the flanking sequences suitably have a length of from about 6 to about 13 nucleotides. The construction of the ribozyme library of the present invention, as shown in FIG. 1, starts out from synthetic oligonucleotides with a random sequence of from about 6 to about 13 nucleotides. These are combined with the ribozyme sequence, converted into a double strand and cloned with flanking restriction sites into the corresponding insertion site of the expression cassette.

Figure 2:
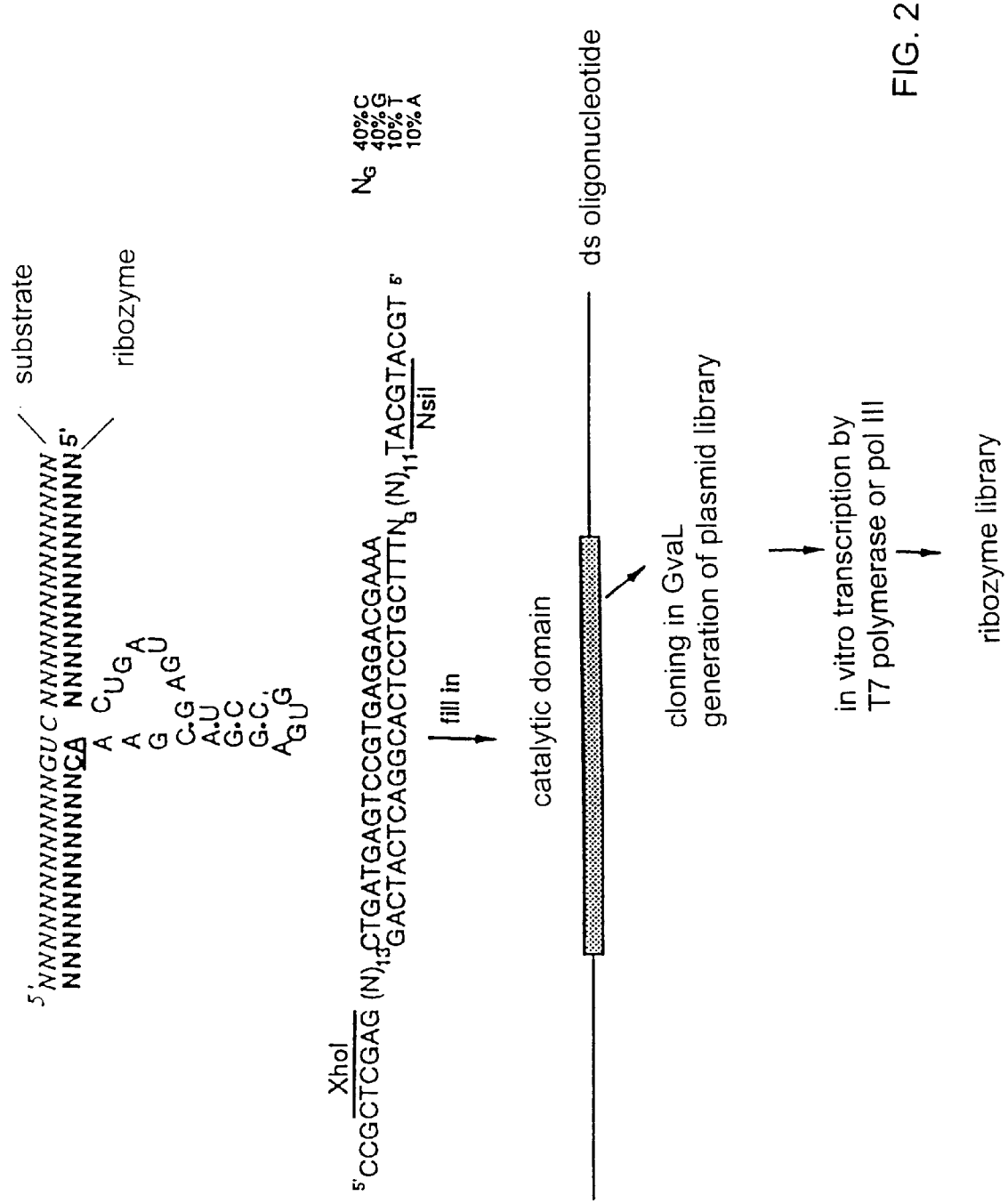
FIG. 2 shows the use of the ribozyme library of the present invention (SEQ ID NO: 5, 7, 8)

In explaining the diagrammatic showing of the use of the ribozyme library of the present invention in FIG. 2, growth hormone can be used as an example. The growth hormone gene has 150 theoretical cleavage sites (ribozyme binding sites, GUC or CUC base sequences). Only some cleavage sites will be accessible in vivo. These and the most effective ribozymes, matching the cleavage sites, are to be isolated.

First a pool of ribozyme genes is synthetically produced for this purpose, a central "hammerhead" ribozyme sequence being flanked by 13 nucleotides of random sequence. These genes are cloned into an expression vector (GvaL) for ribozymes into a sequence coding for the adenoviral va-RNA, allowing for high stability, which is under the control of a T7 promoter, and flanked on both sides by an identical sequence of 21 nucleotides, which are to prevent the formation of a secondary structure. The cloning results in a library of about $10^9$ clones. To isolate a specific ribozyme, the target gene is transcribed in vitro from a suitable construct (with T7-polymerase or RNA polymerase III) and the RNA obtained is incubated with the ribozyme library, which was also transcribed in vitro. Subsequently, the cleavage products are separated electrophoretically. Clearly identifiable fragments are extracted from the gel and sequenced.

The sequence at the ends of the fragments permits the cleavage site to be defined and the ribozyme, responsible for the cleavage site, to be identified. The ribozyme in question is amplified from the ribozyme library using two oligonucleotides specific for its flanking sequences, and cloned once again in the vector GvaL as described below in Example 1. The ribozyme activity of the library is detected by incubation with total cellular or cytoplasmic RNA and its degradation, as described below in Example 2. The presence of ribozymes against a particular target RNA, such as hGH, is detected by incubation with an in vitro transcribed RNA, as described below in Example 3. The cleavage sites are localized by isolating fragments of the cleaved target RNA and sequencing them, as described below in Example 4. The isolation of specific ribozymes is carried out by hybridization with oligonucleotides that are specific for the flanks of the preferred cleavage site, thereby identifying a preselected ribozyme. The specificity and effectiveness of the ribozymes, isolated from the bank and recloned, are determined by their incubation with the target RNA, as described below in Example 5.

The biological effectiveness, that is, the switching off of the function of the target RNA in vivo, is determined by transfection of the recloned ribozyme with the target gene in suitable cells, such as CHO, that means its employment as a stably expressing clone, and subsequent determination of the specific protein synthesis, such as hGH secretion as described below in Example 6. Further details of the invention are described in greater detail and are illustrated in the following examples.

The expression cassette is most suitably a vector for the antisense and for the ribozyme expression. This vector for antisense expression and ribozyme expression can bring about a continuous and stable expression of a particular desired ribozyme or an antisense sequence in a cell. This suitable expression cassette has a strong promoter, suitably a T7 promoter, an adenoviral va-RNA gene, a stable loop region, and an insertion site for the antisense/ribozyme sequence in the loop region.

The T7 promoter is suitably used in combination with T7 polymerase. The loop region is in a restriction site in the central part of the adenoviral va-RNA gene and its size is at least 2×21 bases of identical sequence. A suitable base sequence of the loop region is 5'-AACCCAGGTGTGCGACGTCAG-3' (Seq. Id. No. 10).

The cleavage results of FIG. 7 also show
(A) the structure of the specific ribozyme for a 27 n.t. region about the GUC at position 988 within the exon IV of hGH RNA;
(B) the maps of plasmid matrices for ribozyme synthesis by in vitro transcription with pol III (HeLa extract) and T7 RNA polymerase; and
(C) an electrophoretic representation of the cleavage products.

In an illustrative example of preparing this suitable expression cassette the T7Rz and T7Rzneo plasmids were linearized by a Hind III treatment. GvaRz and GvaLRz were used in circular form. hGH RNA was synthesized from a linear (SstI section) of genomic hGH gene (1663 nt) by in vitro transcription with T7 RNA polymerase (with 0.2 $\mu Ci^{32}P$ of CTP/$\mu$g of RNA). An equimolar mixture (100 nM) of ribozyme and substrate was incubated at 37° C. in 50 mM of Tris-HCl of pH 7.5 and 10 mM of magnesium chloride for 30 minutes with prior heat denaturation (90 seconds at 95° C.). After the cleavage, the RNAs were purified and separated individually on a 6% polyacrylamide gel. Full-length RNA and ribozyme cleavage products (988 nt and 675 nt) were detected. The result shows that the embedding of the catalytic hammerhead structure in a stabilizing RNA (va) leads to a stable ribozyme, capable of functioning, only after the additional incorporation of the loop region.

EXAMPLE 1

Isolation of Specific Ribozymes From the Library

Figure 3:
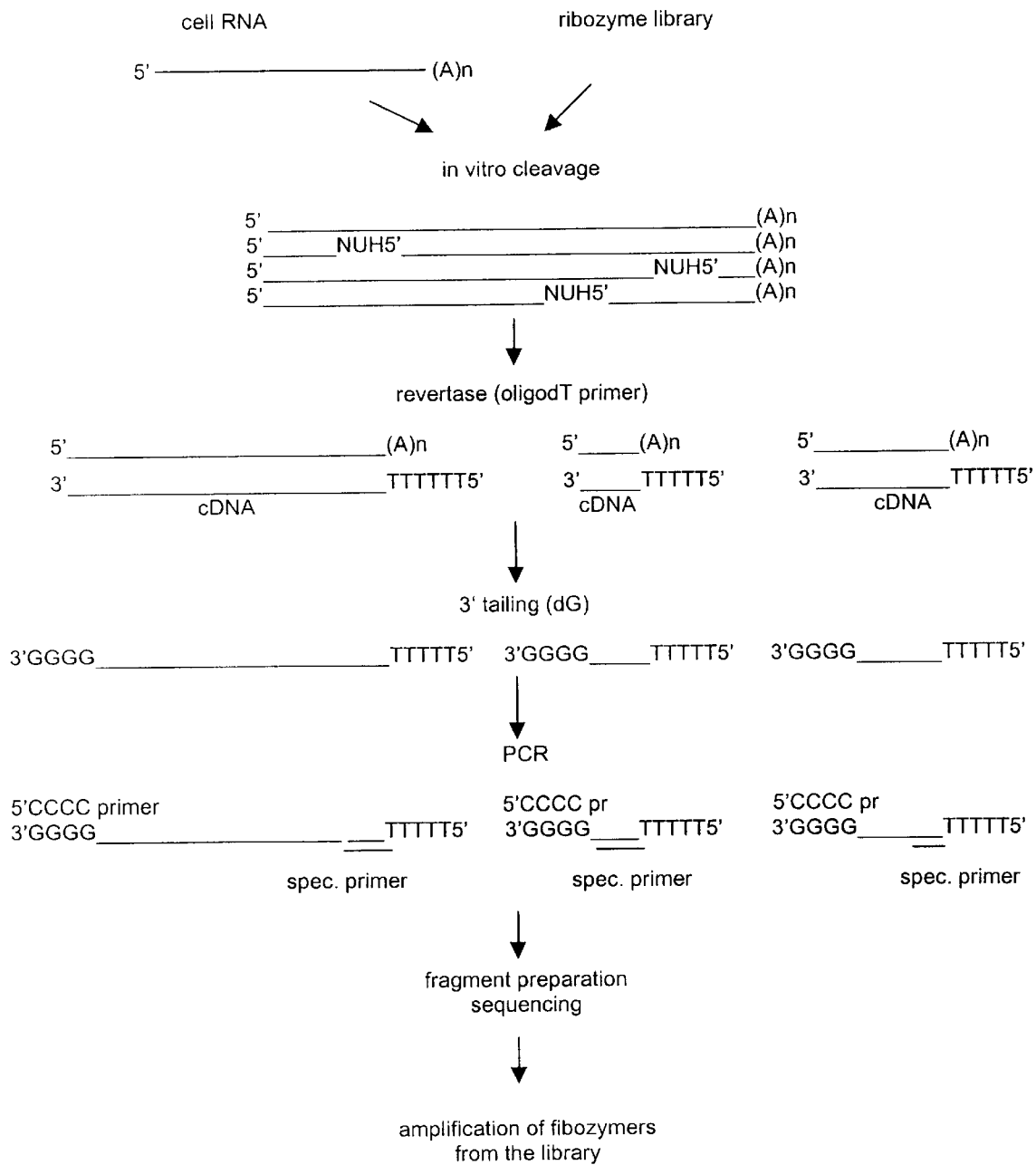
FIG. 3 shows amplification and cloning of ribozyme specific for the human growth hormone (hGH) gene (SEQ ID NO: 9)
Figure 5:
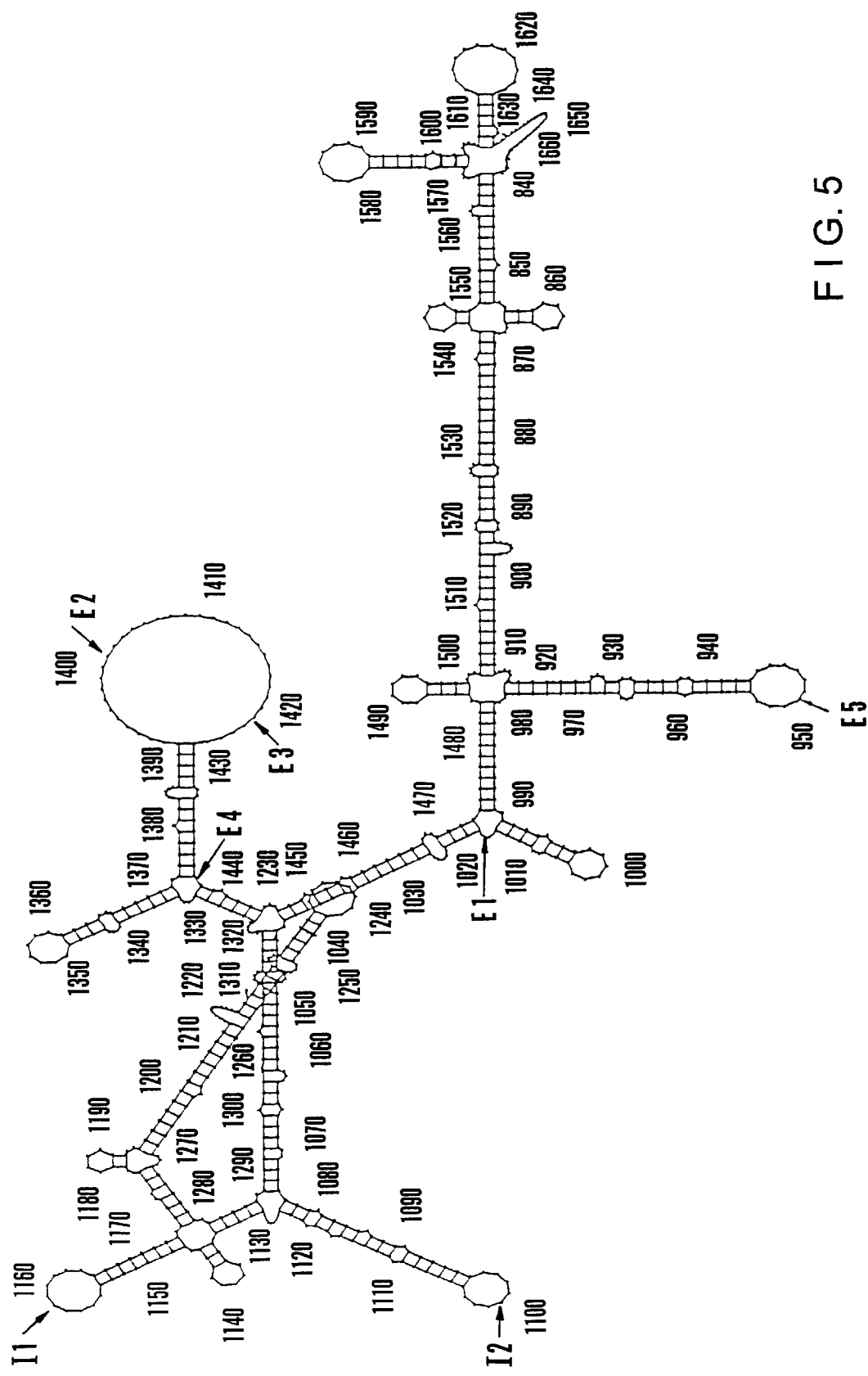
FIG. 5 is a computer representation of the cleavage sites within the secondary structure of the nucleotide sequence of FIG. 4.
Figure 6:
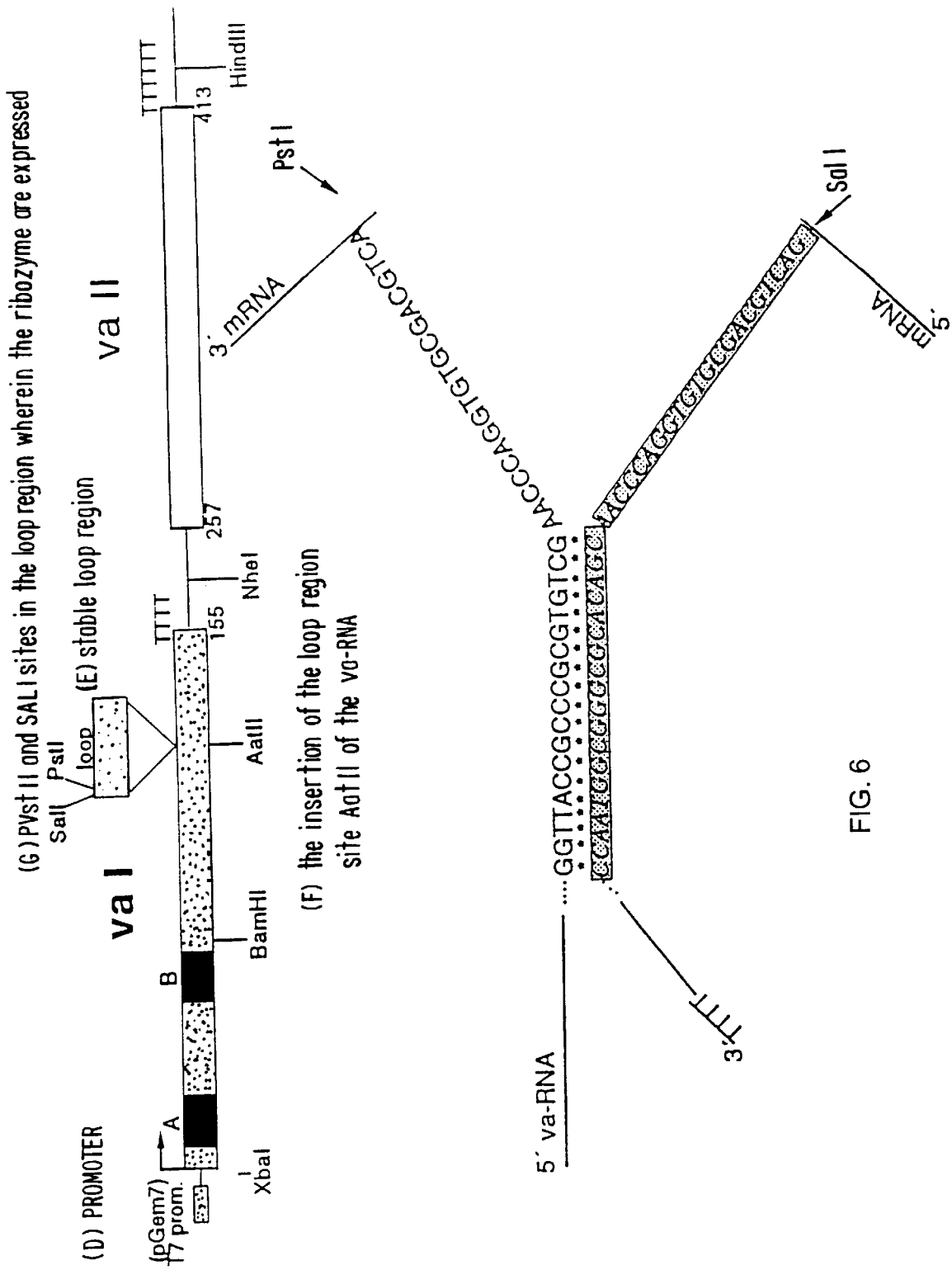
FIG. 6 is an example of an optimized expression cassette (SEQ ID NO: 11)

The strategy is shown diagrammatically in FIGS. 1 and 2. Synthetic ribozyme genes are prepared where the central part codes for the hammerhead ribozyme and both sides are flanked by random sequences ($N_{11}$, $N_{13}$) and a restriction site. The resulting fragment mixture was cloned into the GvaL cassette as an XhoI-NsiI fragment. A library of about $10^9$ different variants was created. The ribozymes were synthesized in vitro either by T-7 polymerase or po III of an HeLa extract using the library as the template. The RNA of CHO cells, which express the hGH gene steadily (5000 RNA copies per cell), was used as target sequence. Purified RNA was incubated with the in vitro transcribed ribozyme library. After purification of the cleavage products on an oligo-dT column, the 5' end of the downstream cleavage products was analyzed by means of the "RACE" technique as follows. After the reverse transcription with oligo-dT primers, the cDNAs were extended at the 3' end with dG, amplified with an oligo-dC and treated with hGH-specific primers, cloned into pGEMT (Promega) and sequenced. The sequences should start directly downstream from NUH identification sites (GUC, CUC) within the hGH RNA. The gene for the ribozyme, which brings about the cleavage of a selected site, was amplified by PCR from the ribozyme-plasmid library, specific, degenerate primers being used for the flanking regions of the ribozyme gene, as shown in the upper part of FIG. 3. After amplification, the resulting fragment was cloned between the PstI and SalI sites of the vector GvaL. As shown at the bottom of FIG. 3, among the sequenced 50 clones, ribozymes with flanks of different length (from about 7 to about 13 nucleotides) were found for three ribozyme cleavage sites.

EXAMPLE 2

Cleavage of Cellular RNA by Transcribed Ribozymes

The cleavage of cellular RNA was carried out at physiological pH (50 mM of Tris-HCl, pH 7.5) at 37° C. for one hour with or without prior heat denaturation (90 seconds at 95° C.) in a 15 $\mu$L reaction vessel. The following formulations were selected:

1./2. Purified total RNA (1 $\mu$g/sample) as target. Ribozyme GvaLRz as T7 transcript; the in vitro transcript of GvaL served as control.
3. Cytoplasmic RNA/protein fraction as target. Cells ($10^5$) were lysed in 50 mM Tris-HCl (pH 7.5) for 10 minutes in ice, frozen in liquid nitrogen and thawed at 37° C.; the nuclei were then removed by centrifugation. A T7 transcript of GvaLRz (10 $\mu$g) was used as ribozyme.
4. Cytoplasmic RNA as target. The ribozyme was prepared by pol III transcription (2 $\mu$g/sample).

The most obvious cleavages were obtained with T7 transcripts and total or also cytoplasmic RNA.

EXAMPLE 3

Specific in vitro Cleavage of hGH mRNA by Ribozymes From the Library

Total or cytoplasmic RNA preparations from hGH-producing cells are incubated with ribozymes from the library, which was transcribed either with pol III or T7 polymerase. hGH-specific 3' fragments are reversely transcribed and amplified by PCR. The PCR conditions are selected so that mainly fragments <1000 bp are formed. PCR products are separated on a 6% polyacrylamide gel; markers for the fragment size are applied on the left track. Six specific bands were found, the corresponding fragment lengths of which correlated with one in 4 exon sites (E1–E4) and 2 intron sites (I1, I2). It may be noted that T7 pol transcripts are more easily detected and that there are more cleavage sites in total RNA than in cytoplasmic RNA.

EXAMPLE 4

Localization of Ribozyme Cleavage Sites Within hGH mRNA

The E1–E4 and I1, I2 fragments are cut out of the gel, purified and cloned into pGEMT. 20 clones were sequenced from each fragment. About 50% of the clones start either at a CUC or a GUC site. The other 50% represent probable degraded RNA products.

According to the sequence of the fragments, the cleavage sites are contained in the sequence of FIG. 4 from hGH, E1: 1017 (exon IV), E2: CTC 1401 (exon V), E3: CTC 1422 (exon V), E4: CTC 1441 (exon V), E5 (originates from a separate experiment): GTC (exon IV), 12: CTC 1099 (intron IV), I1: GTC (intron IV).

The graphic representation was obtained with the HUSAR MFOLD computer program using PLOTFOLD.

EXAMPLE 5

In vitro Cleavage of HGH-Specific RNA by Ribozymes From the Library (A) Cleavage with 3 different, selected ribozymes. The ribozymes are transcribed with T7 polymerase from, in each case, a selected clone and incubated for 20 minutes at 37° C. without heat denaturation with in vitro transcribed hGH RNA of the same molarity (both 100 nM). Samples are applied on a denatured 6% polyacrylamide gel. The resulting fragments have the expected size (El: 1017, 646; II: 1099, 564; E5: 952, 711).

(B) Cleavage of hGH RNA by El ribozyme with complementary regions of different length. The incubation was carried out as in (A). The fragments were separated on a 4% denaturing polyacrylamide gel. As shown on the bottom of FIG. 3, the length of the complementary region of the E1 ribozyme is 26=13/13, 21=10/11 or 15=8/7. The two specific cleavage products can be detected only after incubation with ribozymes in the presence of magnesium. The most effective cleavage is found for the ribozyme with the shortest complementarily (15=8/7).

EXAMPLE 6

Effect of the Ribozyme Expression in vivo on the Level of the hGH Secretion

The transfection of CHO cells took place simultaneously with pCMVhGH, ribozymes or control constructs and pSV2neo. The short-term expression was tested after 3 days and the stable expression after 4 weeks after selection with geneticin. The hGH level was determined with ELISA (limit of detection: 3 ng/mL). The level of hGH obtained with pCMVhGH+Gval was taken to be 100% (short-term: 7 μg of hG/mL/24 hr; stable: 2 μg of hGH/mL/24 hr). A mutant ribozyme (E1 8/7) was used as a control.

The results of a typical experiment are summarized in following table:

| Expression System | pol III short term hGH (%) | pol III stable hGH (%) | T7 pol short term hGH (%) | T7 pol stable hGH (%) |
| --- | --- | --- | --- | --- |
| GvaL | 100 | 100 | 100 | 100 |
| E1 (13/13) | 36 | 85 | 78 | 2 |
| E1 (10/11) | 12 | 50 | — | — |
| E1 (8/7) | 7 | 25 | 75 | 0.2 |
| E1 (8/7) mut. | 95 | 92 | 90 | 87 |
| I1 (8/8) | 42 | 78 | — | — |
| E5 (8/7) | 32 | 50 | — | — |

We claim:

1. A ribozyme library comprising a collection of ribozyme genes encoding a hammerhead structure and flanking sequences of random nucleotides cloned at least once into an expression cassette for ribozyme expression, wherein said expression cassette contains a T7 promoter proximal to the 5' end of said cassette, an adenoviral va-RNA-gene adjacent to said promoter, and a loop region located in the central part of said gene, said loop region defined as a series of adjacent nucleotides between a first nucleotide and a second nucleotide, said first nucleotide further linked on either side to adjacent nucleotides other than the second nucleotide, and the second nucleotide further linked on either side to adjacent nucleotides other than the first nucleotide.

2. The ribozyme library of claim 1, wherein the library contains from about $10^9$ to about $10^{11}$ ribozyme genes.

3. The ribozyme library of claim 1, wherein said hammerhead structure comprises a double stranded DNA having the sequence CTGATGAGTCCGTGAGGACGAAAC (Seq. Id. No. 1).

4. A process for identifying and isolating a ribozyme, comprising incubating with a ribozyme library a DNA or RNA sequence having a predetermined target sequence, said ribozyme library comprising a collection of ribozyme genes encoding a hammerhead structure and flanking sequences of random nucleotides cloned at least once into an expression cassette for ribozyme expression, identifying the resulting cleaved targets, and isolating the cleaving ribozyme.

5. The process of claim 4, wherein said DNA or RNA sequence is an in vitro transcribed RNA, a total-RNA, or a cytoplasmic cell RNA, and said incubating is carried out in the presence of 100 μm of a Mg salt.

6. The process of claim 5, wherein said process for identifying is carried out by a PCR reaction with gene-specific primers, and the isolation of the cleaved targets is carried out by electrophoresis in a gel.

7. The process of claim 5, wherein the ribozyme target RNA is isolated from the cleaved target gel, and identified by sequencing of the cleavage sites.

8. The process of claim 4, wherein a preselected ribozyme is isolated from the library by hybridization with two oligonucleotides that are specific for the preselected ribozyme, and the isolated ribozyme is employed as an expression clone.

* * * * *

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: rRNA (xi) SEQUENCE DESCRIPTION: SEQ ID NO: 1:

CTGATGAGTC CGTGAGGACG AAAC      24

(2) INFORMATION FOR SEQ ID NO: 2:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: rRNA (xii) SEQUENCE DESCRIPTION: SEQ ID NO: 2:

GTGTACGGCG CCTCTGACAG CAACGTC      27

(2) INFORMATION FOR SEQ ID NO: 3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: rRNA (xi) SEQUENCE DESCRIPTION: SEQ ID NO: 3:

AGGCGCCGNN NNNTACGTCG T                              21

(2) INFORMATION FOR SEQ ID NO: 4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: rRNA (xi) SEQUENCE DESCRIPTION: SEQ ID NO: 4:

CGCTCGAGNN NNNNGCTGTC A                              21

(2) INFORMATION FOR SEQ ID NO: 5:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: rRNA (xi) SEQUENCE DESCRIPTION: SEQ ID NO: 5:

CAGCTCGACG TTGCTGTCAA GGCGCCGTAC ACATGCAG                38

(2) INFORMATION FOR SEQ ID NO: 6:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: rRNA (xi) SEQUENCE DESCRIPTION: SEQ ID NO: 6:

CAGCTCACCG TTGCTGTCAA GGCGCCGTAA GAATGCAG                38

(2) INFORMATION FOR SEQ ID NO: 7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: rRNA (xi) SEQUENCE DESCRIPTION: SEQ ID NO: 7:

CCGCTCGAGC TGATGAGTCC GTGAGGACGA AA                      32

(2) INFORMATION FOR SEQ ID NO: 8:

(i) SEQUENCE CHARACTERISTICS:
        (A) LENGTH: 32 base pairs (B) TYPE: nucleic acid
            (C) STRANDEDNESS: single
            (D) TOPOLOGY: linear (ii) MOLECULE TYPE: rRNA (xi) SEQUENCE DESCRIPTION: SEQ ID NO: 8:

```
TGCATGCATT TTCGTCCTCA CGGACTCATC AG                                      32
```

(2) INFORMATION FOR SEQ ID NO: 9:

(i) SEQUENCE CHARACTERISTICS:
            (A) LENGTH: 792 base pairs
            (B) TYPE: nucleic acid
            (C) STRANDEDNESS: single
            (D) TOPOLOGY: linear (ii) MOLECULE TYPE: rRNA (xi) SEQUENCE DESCRIPTION: SEQ ID NO: 9:

```
AGGCGGGGAT GGGGGAGACC TGTAGTCAGA GCCCCCGGGC AGCACAGCCA ATGCCCGTCC         60
TTGCCCCTGC AGAACCTAGA GCTGCTCCGC ATCTCCCTGC TGCTCATCCA GTCGTGGCTG        120
GAGCCCGTGC AGTTCCTCAG GAGTGTCTTC GCCAACAGCC TGGTGTACGG CGCCTCTGAC        180
AGCAACGTCT ATGACCTCCT AAAGGACCTA GAGGAAGGCA TCCAAACGCT GATGGGGGTG        240
AGGGTGGCGC CAGGGGTCCC CAATCCTGGA GCCCCACTGA CTTTGAGAGA CTGTGTTAGA        300
GAAACACTGG CTGCCCTCTT TTTAGCAGTC AGGCCCTGAC CCAAGAGAAC TCACCTTATT        360
CTTCATTTCC CCTCGTGAAT CCTCCAGGCC TTTCTCTACA CTGAAGGGGA GGGAGGAAAA        420
TGAATGAATG AGAAAGGGAG GGAACAGTAC CCAAGCGCTT GGCCTCTCCT TCTCTTCCTT        480
CACTTTGCAG AGGCTGGAAG ATGGCAGCCC CCGGACTGGG CAGATCTTCA AGCAGACCTA        540
CAGCAAGTTC GACACAAACT CACACAACGA TGACGCACTA CTCAAGAACT ACGGGCTGCT        600
CTACTGCTTC AGGAAGGACA TGGACAAGGT CGAGACATTC CTGCGCATCG TGCAGTGCCG        660
CTCTGTGGAG GGCAGCTGTG GCTTCTAGCT GCCCGGGTGG CATCCCTGTG ACCCCTCCCC        720
AGTGCCTCTC CTGGCCCTGG AAGTTGCCAC TCCAGTGCCC ACCAGCCTTG TCCTAATAAA        780
ATTAAGTTGC AT                                                           792
```

(2) INFORMATION FOR SEQ ID NO: 10:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: rRNA (xi) SEQUENCE DESCRIPTION: SEQ ID NO: 10:

```
AACCCAGGTG TGCGACGTCA G                                                  21
```

(2) INFORMATION FOR SEQ ID NO: 11:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: rRNA (xii) SEQUENCE DESCRIPTION: SEQ ID NO:11:

-continued

```
GGTTACCGCC CGCGTGTCGA ACCCAGGTGT GCGACGTCAG                    40

(2) INFORMATION FOR SEQ ID NO: 12:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: rRNA (xi) SEQUENCE DESCRIPTION: SEQ ID NO: 12:

UCCUCAGGAG UGGUCUUCGC CAACAGCC                                 28
```